United States Patent [19]  [11]  4,116,668
Gaughan et al.  [45]  Sep. 26, 1978

[54] N-CARBAMOYL ETHYL OXANILATES

[75] Inventors: Edmund J. Gaughan, Berkeley; George B. Large, Orinda, both of Calif.

[73] Assignee: Stauffer Chemical Company, Westport, Conn.

[21] Appl. No.: 839,131

[22] Filed: Oct. 3, 1977

Related U.S. Application Data

[60] Division of Ser. No. 759,206, Jan. 13, 1977, Pat. No. 4,068,097, which is a division of Ser. No. 638,491, Dec. 8, 1975, Pat. No. 4,018,813, which is a continuation of Ser. No. 559,104, Mar. 17, 1975, abandoned.

[51] Int. Cl.² .......................... A01N 9/20; A01N 9/22; A01N 9/28
[52] U.S. Cl. ........................................ 71/88; 71/94; 71/95; 71/111
[58] Field of Search ....................... 71/88, 94, 95, 111

[56] References Cited
U.S. PATENT DOCUMENTS

| 3,210,369 | 10/1965 | Smith et al. | 560/43 |
| 3,539,618 | 11/1970 | Stoffel | 71/111 |
| 3,907,544 | 9/1975 | Olin | 71/118 |

Primary Examiner—Catherine L Mills
Attorney, Agent, or Firm—M. Henry Heines

[57] ABSTRACT

A composition of matter is described herein which has herbicidal activity and methods of use. The composition is defined by the following generic formula

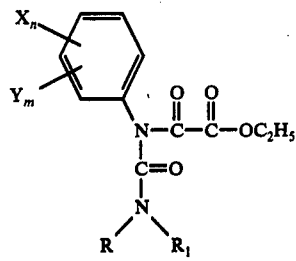

wherein X and Y are independently selected from the group consisting of chloro, bromo, and trifluoromethyl; $n$ is either 0 or 1; $m$ is either 0 or 1; and R and $R_1$ are independently selected from the group consisting of lower alkyl from $C_1$ to $C_3$, inclusive, and lower alkoxy from $C_1$ to $C_3$, inclusive, or R and $R_1$ taken together is selected from the group consisting of

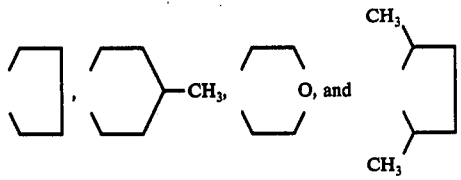

17 Claims, No Drawings

N-CARBAMOYL ETHYL OXANILATES

CROSS REFERENCE TO RELATED APPLICATION

This is a division, of application Ser. No. 759,206, filed Jan. 13, 1977 now U.S. Pat. No. 4,068,097 which is a divisional of application Ser. No. 638,491, filed Dec. 8, 1975, now U.S. Pat. No. 4,018,813, which in turn is a continuation-in-part application of Ser. No. 559,104, filed Mar. 17, 1975, now abandoned.

BRIEF DESCRIPTION AND BACKGROUND OF THE INVENTION

This invention relates to a class of substituted ethyl oxanilates and to their use as herbicides. More specifically, this invention relates to N-(carbamoyl) ethyl oxanilates, which are represented by the formula.

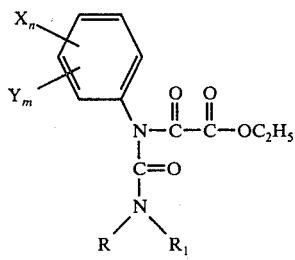

wherein X and Y are independently selected from the group consisting of chloro, bromo and trifluoromethyl; $n$ is either 0 or 1; $m$ is either 0 or 1; and R and $R_1$ are independently selected from the group consisting of lower alkyl from $C_1$ to $C_3$, inclusive, and lower alkoxy from $C_1$ to $C_3$, inclusive, or R and $R_1$ taken together is selected from the group consisting of

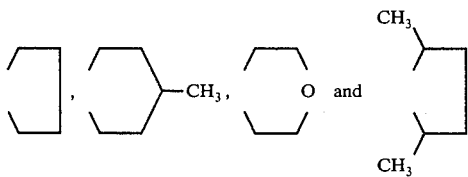

Because of the N-(carbamoyl) substitution, the generic structure of the compound of this invention is similar to that of a tetra-substituted urea. An example of such a urea teaching a monocarbonyl radical bonded to a nitrogen atom which is also bonded to a halogenated phenyl radical is described in French Pat. No. 1,250,422. The compound of the present invention differs from that described in the above-mentioned patent in that it teaches the preparation and herbicidal use of a variety of oxanilates which, because of their characteristic adjacent pair of carbonyl groups, are beyond the scope of the above-mentioned patent.

DETAILED DESCRIPTION OF THE INVENTION

In the practice of the present invention, the novel compounds of the present invention are manufactured by reacting the properly selected 1,3,3-trisubstituted urea with sodium hydride and then reacting the resulting sodium salt of the urea with ethyloxalyl chloride to obtain the N-(carbamoyl) ethyl oxanilate, as shown in the examples herein. Following the examples of preparation is a table of compounds which are prepared according to the procedures described herein. Compound numbers have been assigned to them and are used for identification throughout the balance of the specification. These compounds are used as herbicides and can be applied by methods and means as hereinafter disclosed.

EXAMPLE 1

N-(dimethylcarbamoyl) ethyl-3'-trifluromethyl oxanilate.

Sodium hydride (21.6 g., 9 mole) was suspended in 300 ml. of tetrahydrofuran (dried over molecular sieve) and a solution of 1-(m-trifluoromethylphenyl)-3,3-dimethyl urea (191 g., 0.823 mole) in 1700 ml. dry tetrahydrofuran was added dropwise under argon at room temperature. The mixture was stirred one hour at room temperature and one hour at 40°–45° C. The solution was decanted under argon and added dropwise to a solution of ethyloxalyl chloride 120 g., (0.88 mole) in 200 ml. of tetrahydrofuran. During the addition, the reactor was cooled with water to maintain the reactor temperature at 43° C or below. A precipitate appeared and the mixture was stirred approximately 16 hours at room temperature, then stirred for 1 hour at 45° C. The volatiles were removed from the reaction mixture in vacuo. The residue was dissolved in 600 ml. of benzene and 200 ml. of 5% sodium bicarbonate solution. The organic layer was washed with 200 ml. additional bicarbonate solution and dried over magnesium sulfate. The solvent was removed in vacuo and the remaining crude product was recrystallized from a benzene-hexane mixture. The yield of the product was 175.7 g. of 65% of theory. The melting point was 67°–69° C. The structure of the product was confirmed by infrared and NMR spectra.

EXAMPLE 2

N-(dimethylcarbamoyl)-ethyl-3',4'-dichlorooxanilate.

Sodium hydride (24.5 g., 1.02 moles) was suspended in 300 ml. of dry tetrahydrofuran. 217 g. (0.93 mole) of 1-(3,4-dichlorophenyl)-3,3-dimethyl urea in 1600 ml. of tetrahydrofuran was added dropwise to the sodium hydride under argon at room temperature. The mixture was then stirred for 1 hour at room temperature and for another hour at 40°–45° C. The solution was transferred under argon to an addition funnel and added dropwise to 136.5 g. (1.0 mole) of ethyloxalyl chloride which was dissolved in 180 ml. tetrahydrofuran. The temperature was allowed to rise at 43° C. The mixture was then stirred for 2 hours at room temperature, followed by 1.5 hours at 40°–45° C., and finally approximately 16 hours at room temperature. The volatiles were removed in vacuo and the residue was treated with 800 ml. of benzene and 400 ml. of 5% sodium bicarbonate solution. The insoluble material was filtered, washed with benzene, and dried. The original benzene filtrate was washed with two further 200 ml. portions of 5% sodium bicarbonate solution and dried over magnesium sulfate. This solution was concentrated in vacuo, filtered, and the filter cake washed with hexane and dried. This was combined with the original filter cake to give 249.8 g. (80% of theoretical yield) of product with a melting point of 123°–124° C. The structure of the product was confirmed by infrared and NMR spectra.

TABLE I

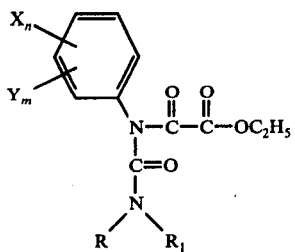

| Compound No. | n | X | m | Y | R | R₁ | $n_D^{30}$, m.p. or Description |
|---|---|---|---|---|---|---|---|
| 1 | 0 | — | 1 | 4-Cl | CH₃ | CH₃ | 1.5327 |
| 2 | 1 | 3-Cl | 1 | 4-Cl | CH₃ | CH₃ | 108–114° C |
| 3 | 0 | — | 1 | 3-CF₃ | CH₃ | CH₃ | semi-solid |
| 4 | 1 | 3-Cl | 1 | 5-Cl | (cyclopentyl) | | semi-solid |
| 5 | 1 | 3-Cl | 1 | 4-Cl | OCH₃ | CH₃ | viscous oil |
| 6 | 1 | 3-Cl | 1 | 4-Br | OCH₃ | CH₃ | 1.5303 |
| 7 | 1 | 3-Cl | 1 | 4-Cl | (4-methylcyclohexyl) | | semi-solid |
| 8 | 1 | 3-Cl | 1 | 4-Cl | (tetrahydropyranyl) | | 96–99° C |
| 9 | 1 | 3-Cl | 1 | 4-Cl | CH₃, (4-methylcyclopentyl-CH₃) | | 1.5170 |

HERBICIDAL SCREENING TESTS

As previously mentioned, the herein described compounds produced in the above-described manner are phytotoxic compounds which are useful and valuable in controlling various plant species. Compounds of this invention are tested as herbicides in the following manner.

Pre-emergence Herbicide Screening Test

Using an analytical balance, 20 mg. of the compound to be tested is weighed out on a piece of glassine weighing paper. The paper and compound are placed in a 30 ml. wide-mouth bottle and 3 ml. of acetone containing 1% Tween 20 ® (polyoxyethylene sorbitan monolaurate) is added to dissolve the compound. If the material is not soluble in acetone, another solvent such as water, alcohol or dimethylformamide (DMF) is used instead. When DMF is used, only 0.5 ml. or less is used to dissolve the compound and then another solvent is used to make the volume up to 3 ml. The 3 ml. solution is sprayed uniformly on the soil contained in a small flat one day after planting weed seeds in the flat of soil. An atomizer is used to apply the spray using compressed air at a pressure of 5 lb/sq. inch. The rate of application is 8 lb/acre and the spray volume is 143 gallons per acre.

On the day preceeding treatment, the flat which is 7 inches long, 5 inches wide and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. Ample seeds are planted to give about 20 to 50 seedlings per row after emergence depending on the size of the plants.

The seeds used are foxtail (*Setaria spp.*), watergrass (*Echinochloa crusgalli*), red oat (*Avena sativa*), redroot pigweed (*Amaranthus retroflexus*), mustard (*Brassica juncea*), curly dock (*Rumex crispus*), and hairy crabgrass (*Digitaria sanguinalis*).

After treatment, the flats are placed in the greenhouse at a temperature of 70° to 85° F and watered by sprinkling. Two weeks after treatment, the degree of injury or control is determined by comparison with untreated check plants of the same age. The injury rating from 0 to 100% is recorded for each species as percent control with 0% representing no injury and 100% representing complete kill.

Post-emergence Herbicide Screening Test

Seeds of six plant species, including hairy crabgrass, watergrass, red oat, mustard, curly dock and Pinto beans (*Phaseolus vulgaris*), are planted in the flats as described above for pre-emergence screening. The flats are placed in the greenhouse at 70° to 85° F and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg. of the test compound, dissolving it in 5 ml. of acetone containing 1% Tween 20 ® (polyoxyethylene sorbitan monolaurate) and then adding 5 ml. of water. The solution is sprayed on the foliage using an atomizer at an air pressure of 5 lb/sq. inch. The spray concentration is 0.2% and the rate is 8 lb/acre. The spray volume is 476 gallons per acre.

The results of these tests are shown in Table II.

TABLE II
HERBICIDAL ACTIVITY - SCREENING RESULTS
PER CENT CONTROL AT 8 LB/A

| Compound Number | Pre-emergence (Average of 7 plant species) | Post-emergence (Average of 6 plant species) |
|---|---|---|
| 1 | 98 | 99 |
| 2 | 99 | 100 |
| 3 | 99.6 | 100 |
| 4 | 0 | 44 |
| 5 | 100 | 99 |
| 6 | 94 | 100 |
| 7 | 26 | 92 |
| 8 | 55 | 96 |
| 9 | 57 | 87 |

The compounds of the present invention are used as pre-emergence or post-emegence herbicides and are applied in a variety of ways at various concentrations. In practice, the compounds are formulated with an inert carrier, utilizing methods well known to those skilled in the art, thereby making them suitable for application as dusts, sprays, or drenches and the like, in the form and manner required. The mixtures can be dispersed in water with the aid of a wetting agent or they can be employed in organic liquid compositions, oil and water, water in oil emulsions, with or without the addition of wetting, dispersing or emulsifying agents. An herbicidally effective amount depends upon the nature of the seeds or plants to be controlled and the rate of application varies from 0.10 to approximately 50 pounds per acre. The concentration of a compound of the present invention, constituting an effective amount in the best mode of administration in the utility disclosed, is readily determinable by those skilled in the art.

The phytotoxic compositions of this invention employing an herbicidally effective amount of the comound described herein are applied to the plants in the conventional manner. Thus, the dusts and liquid compositions can be applied to the plant by the use of power dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles and these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxy-propylamino)-6-methyl-thio-s-triazine; 2-chloro-4-ethylamino-6-isopropylamino-s-triazine, and 2-ethylamino-4-isopropylamino-6-methyl-mercapto-s-triazine, urea derivatives, such as 3-(3,4-dichlorophenyl)-1,1-dimethyl urea and acetamides such as N,N-di-allyl-α-chloroacetamide, N-(α-chloroacetyl) hexamethyleneimine, and N,N-diethyl-α-bromoacetamide, and the like; benzoic acids such as 3-amino-2,5-dichlorobenzoic; S-ethyldipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

Various changes and modifications are possible without departing from the spirit and scope of the invention described herein and will be apparent to those skilled in the art to which it pertains. It is accordingly intended that the present invention shall be limited only by the scope of the claims.

What is claimed is:

1. The method of controlling undesirable vegetation comprising applying to the locus where control is desired a phytotoxic amount of a compound having the formula

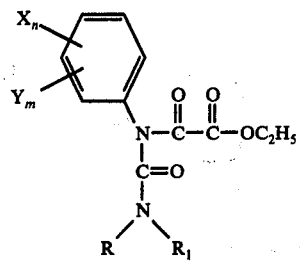

wherein X and Y are independently selected from the group consisting of chloro, bromo and trifluoromethyl; n is either 0 or 1; m is either 0 or 1; and R and $R_1$ are independently selected from the group consisting of lower alkyl from $C_1$ to $C_3$, inclusive; and lower alkoxy from $C_1$ to $C_3$, inclusive, or R and $R_1$ taken together is selected from the group consisting of

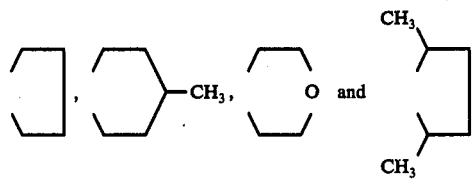

2. A method according to claim 1 in which Y is chloro, n is 0, m is 1, and R and $R_1$ are independently lower alkyl.

3. A method according to claim 2 in which Y is 4-chloro, and R and $R_1$ are each methyl.

4. A method according to claim 1 in which Y is trifluoromethyl, n is 0, m is 1, and R and $R_1$ are independently lower alkyl.

5. A method according to claim 4 in which Y is 3-trifluoromethyl, and R and $R_1$ are each methyl.

6. A method according to claim 1 in which X is chloro, Y is chloro, n is 1, m is 1, and R and $R_1$ are independently lower alkyl.

7. A method according to claim 6 in which X is 3-chloro, Y is 4-chloro, and R and $R_1$ are each methyl.

8. A method according to claim 1 in which X and Y are independently selected from the group consisting of chloro and bromo, n is 1, m is 1, R is alkyl and $R_1$ is alkoxy.

9. A method according to claim 8 in which X is 3-chloro, Y is 4-bromo, R is methyl and $R_1$ is methoxy.

10. A method according to claim 8 in which X is 3-chloro, Y is 4-chloro, R is methyl and $R_1$ is methoxy.

11. A method according to claim 1 in which R and $R_1$ taken together is

X is chloro, Y is chloro, n is 1, and m is 1.

12. A method according to claim 11 in which X is 3-chloro, and Y is 5-chloro.

13. A method according to claim 1 in which R and $R_1$ taken together is

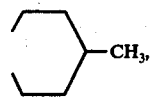
X is chloro, Y is chloro, $n$ is 1, and $m$ is 1.
14. A method according to claim 13 in which X is 3-chloro, and Y is 4-chloro.
15. A method according to claim 1 in which R and $R_1$ taken together is
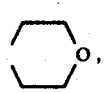
X is chloro, Y is chloro, $n$ is 1 and $m$ is 1.
16. A method according to claim 15 in which X is 3-chloro and Y is 4-chloro.
17. A method according to claim 1 in which R and $R_1$ taken together is
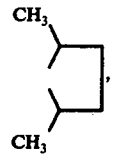
X is 3-chloro, Y is 4-chloro, $n$ is 1 and $m$ is 1.
* * * * *